US00PP25241P2

(12) United States Plant Patent
Danziger

(10) Patent No.: US PP25,241 P2
(45) Date of Patent: Jan. 20, 2015

(54) ***COREOPSIS* PLANT NAMED 'DECOREO16'**

(50) Latin Name: *Coreopsis grandiflora*
Varietal Denomination: DECOREO16

(71) Applicant: Gavriel Danziger, Moshav Mishmar Hashiva (IL)

(72) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 0 days.

(21) Appl. No.: 13/986,006

(22) Filed: Mar. 22, 2013

(51) Int. Cl.
*A01H 5/00* (2006.01)

(52) U.S. Cl.
USPC ..... Plt./417

(58) Field of Classification Search
USPC ..... Plt./417
See application file for complete search history.

*Primary Examiner* — June Hwu
*Assistant Examiner* — Keith Robinson
(74) *Attorney, Agent, or Firm* — Cassandra Bright

(57) ABSTRACT

A new and distinct *Coreopsis* cultivar named 'DECOREO16' is disclosed, characterized by early blooming of fully double flowers that are all at the same height. The new variety has very compact and mounded habit and short peduncles. The new variety is a *Coreopsis*, normally produced as an outdoor garden or container plant.

2 Drawing Sheets

Figure 1:
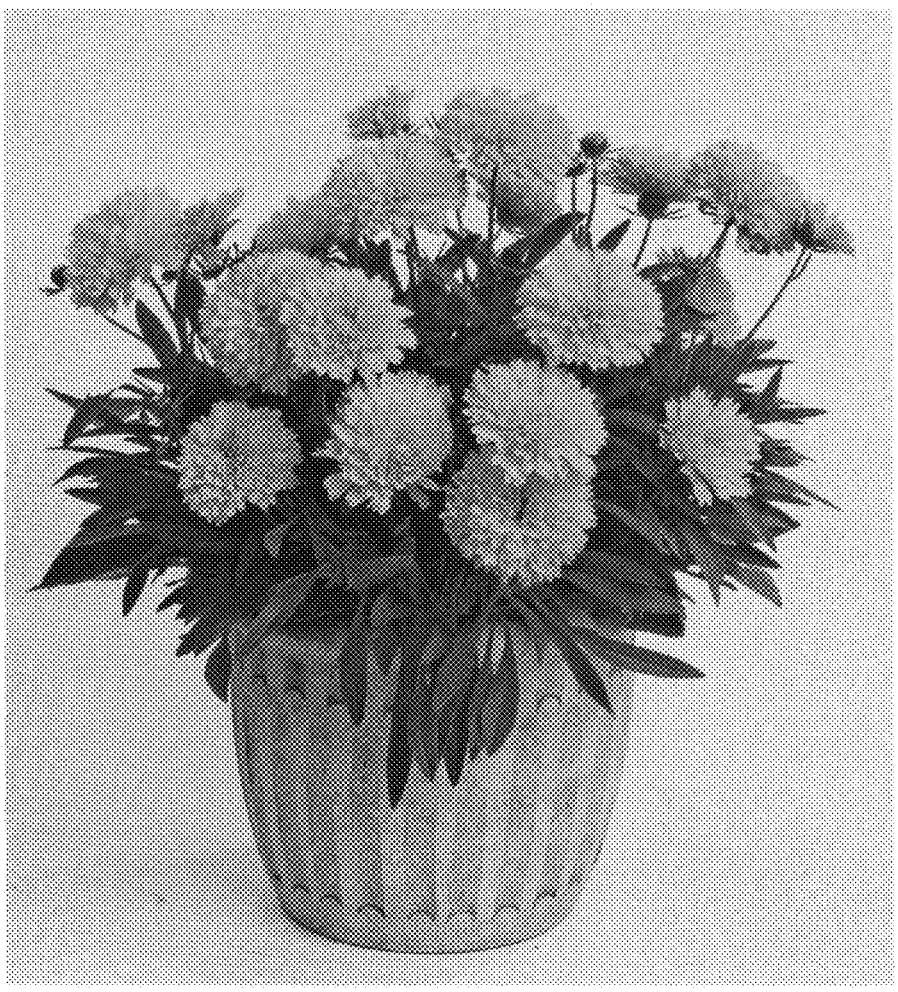

Latin name of the genus and species: *Coreopsis grandiflora.*

Variety denomination: 'DECOREO16'.

BACKGROUND OF THE INVENTION

The new *Coreopsis* cultivar is a product of a planned breeding program conducted by the inventor, Gavriel Danziger, in Moshav Mishmar Hashiva, Israel. The objective of the breeding program was to produce new *Coreopsis* varieties for ornamental commercial applications. The cross resulting in this new variety was made during July of 2009.

The seed parent is the unpatented, proprietary seedling variety referred to as *Coreopsis grandiflora* 'co-9-564' The pollen parent is unknown as it was an open pollination breeding program. The new variety was discovered in July of 2010 by the inventor in a group of seedlings resulting from the 2009 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in February of 2011 and has shown that the unique features of this cultivar are stable and reproduced true to type in more than 100 successive generations.

SUMMARY OF THE INVENTION

The cultivar 'DECOREO16' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DECOREO16' These characteristics in combination distinguish 'DECOREO16' as a new and distinct *Coreopsis* cultivar:

1. Very compact and mounded habit.
2. Early flowering.
3. Short peduncle.
4. Perfect fully doubled flower.
5. All the flowers are of similar height.

Plants of the new cultivar 'DECOREO16' are similar to plants of the seed parent, *Coreopsis grandiflora* 'co-9-564' in most horticultural characteristics, however, plants of the new cultivar 'DECOREO16' produces a fully double flower compared to the semi double flower of seed parent 'co-9-564'. Additionally 'DECOREO16' produces a more compact plant habit as well as shorter peduncles and blooms earlier than seed parent 'co-9-564'.

COMMERCIAL COMPARISON

Plants of the new cultivar 'DECOREO16' are comparable to the variety *Coreopsis* 'Sundancer' U.S. Plant Pat. No. 7,823. The two *Coreopsis* varieties are similar in most horticultural characteristics; however, the new variety 'DECOREO16' differs in producing a more compact and mounded plant habit and fully double flowers compared to the spreading plant habit and semi double flowers of the comparator. Additionally, 'DECOREO16' produces a shorter peduncle than those of the comparator.

Plants of the new cultivar 'DECOREO16' are comparable to the variety *Coreopsis* 'Walcoreop' U.S. Plant Pat. No. 10,299. The two *Coreopsis* varieties are similar in most horticultural characteristics; however, the new variety 'DECOREO16' differs in producing a more compact and mounded plant habit and fully double flowers compared to the spreading plant habit and semi double flowers of the comparator. Additionally, 'DECOREO16' produces a shorter peduncle than those of the comparator.

BRIEF DESCRIPTION OF THE PHOTOGRAPHS

The accompanying photograph in FIG. 1 illustrates in full color a typical plant of 'DECOREO16' grown in a greenhouse, in a 12 cm pot. Age of the plant photographed is approximately 8 weeks from a rooted cutting.

Figure 2:
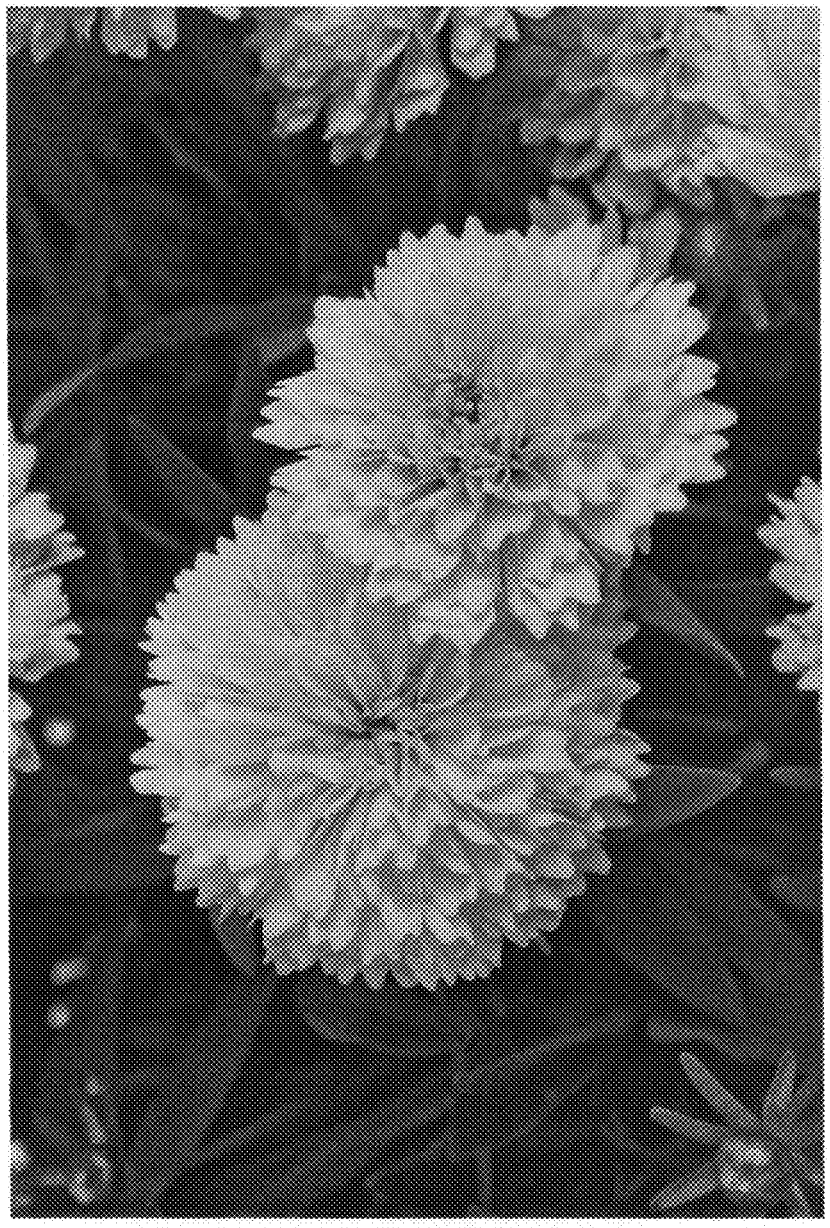

FIG. 2 illustrates in full color a close up of a typical bloom of 'DECOREO16'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DECOREO16' plants grown outdoors during March through August in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types.

Botanical classification: *Coreopsis grandiflora* 'DECOREO16'.

PROPAGATION

Time to initiate roots: Summer: About 3 to 4 days. Winter: About 4 to 5 days.

Root description: Fleshy, branching.

PLANT

Age of plant described: Approximately 12 weeks from rooted cutting.

Pot size of plant described: 12 cm.

Growth habit: Compact and upright, mounded.

Height: Approximately 20 cm.

Plant spread: Approximately 30 cm.

Growth rate: Moderate.

Branching characteristics: Well branched, basal branching.

Length of lateral branches: Approximately 10-15 cm.

Diameter of lateral branches: Approximately 0.3 cm.

Texture of lateral branches: Smooth, glossy, with very light and delicate hair. Slightly ribbed longwise.

Internode length: Approximately 1.5-2.5 cm.

Strength of stem: Flexible, not easily breakable.

Color of lateral branches: Near Yellow-green 151A RHS.

Aspect/angle of branches: 45 degrees upwards from primary branch.

Number of leaves per lateral branch: Approximately 15-20.

FOLIAGE

Leaf:

*Arrangement*.—Opposite.

*Average length*.—Approximately 6-9 cm.

*Average width*.—Approximately 1-1.5 cm.

*Shape of blade*.—Oblanceolate (inversely lance-shaped).

*Apex*.—Rounded.

*Base*.—Wedge-shaped.

*Attachment*.—Absent.

*Margin*.—Entire.

*Texture of top surface*.—Smooth, with very light and delicate hair.

*Texture of bottom surface*.—Smooth, with very light and delicate hair.

*Appearance top surface*.—Matte.

*Appearance bottom surface*.—Matte.

*Leaf internodes length*.—Absent.

*Color*.—Young foliage upper side: Near Yellow-green 144A RHS. Young foliage under side: Near Yellow-green 146C RHS. Mature foliage upper side: Near Green group 137C RHS. Mature foliage under side: Near Green group 138C RHS.

*Venation*.—Type: Reticulate. Venation color upper side: Near Yellow-green 145 C RHS. Venation color under side: Near Yellow-green 146 C RHS.

Petiole:

*Petiole*.—Absent.

FLOWER

Bloom period: From spring until summer (long days).

Other cultural improvements or features: Large fully doubled flower on a strong and short stem.

Bud:

*Bud shape*.—Oblate.

*Bud length*.—Approximately 1-1.5 cm.

*Bud diameter*.—Approximately 1 cm.

*Bud color*.—Near Yellow-green 148A RHS.

Inflorescence: Solitary, fully doubled flower.

*Form*.—Composite. — Tubular flower.

Flower:

*Diameter of entire flower*.—Approximately 6 cm.

*Depth of flower*.—Approximately 5 cm.

*Diameter of disc*.—Absent, it is a fully double flower.

Ray florets:

*Number of ray florets*.—Avg. 120.

*Length*.—Approximately 2.5 cm.

*Width*.—Approximately 1 cm.

*Apex shape*.—Rounded.

*Margin*.—Entire.

Color:

*Ray florets*.—Upper surface at first opening: Near Yellow-orange 15A RHS. Upper surface at maturity: Near Yellow-orange 14A RHS. Upper surface at fading: No fading. Under surface at first opening: Near Yellow-orange 14C RHS. Under surface at maturity: Near Yellow-orange 14C RHS. Under surface at fading: No fading.

*Disc florets*.—Number of Disc Florets: No disk florets — it's a fully double flower.

*Fragrance*.—Light fragrance of Argyranthemum.

Phyllaries/involucral bracts:

*Number*.—8 sepals attached to the petals and 8 sepals opposite to the petals.

*Sepal length*.—Attached sepal: 1 cm and opposite sepal 1.2 cm.

*Sepal width*.—Attached sepal: 0.6 cm and opposite sepal 0.3 cm.

*Sepal texture*.—Smooth.

*Apex shape*.—Attached sepal: pointed and opposite sepal: rounded.

*Margin*.—Color: Attached sepal: near Green 137C RHS and opposite sepal: near Yellow-green 153A RHS.

Peduncle:

*Peduncle length*.—Approximately 10 cm.

*Peduncle diameter*.—Approximately 0.3 cm.

*Angle*.—Approximately 90 degree from center of whorl.

*Color*.—Near Yellow-green 146B RHS.

*Peduncle texture*.—Smooth, slightly ribbed longwise.

REPRODUCTIVE ORGANS

Disc florets: No disk florets — it's a fully double flower.

Ray florets:

*Androecium*.—Absent.

*Gynoecium*.—Pistil number: 60. Pistil shape: Linear. Pistil length: Approx. 1 cm. Style length: Approx. 0.7 cm. Style color: Near Yellow-green 144B RHS. Stigma shape: V shaped. Stigma color: Near Yellow-green 144B RHS. Ovary diameter: 0.2 cm. Ovary color: Near Yellow-green 145 A RHS.

OTHER CHARACTERISTICS

Drought tolerance and cold tolerance: Tolerant of hot, humid summer climates, USDA ZONE: 5.

Fruit/seed production: Not observed.

What is claimed is:

1. A new and distinct cultivar of *Coreopsis* plant named 'DECOREO16' as herein illustrated and described.

* * * * *